United States Patent [19]

Speece

[11] Patent Number: 4,785,801

[45] Date of Patent: Nov. 22, 1988

[54] VERTEBRAE AND RIB MANIPULATION DEVICE

[76] Inventor: Conrad A. Speece, 10477 Silverock Dr., Dallas, Tex. 75218

[21] Appl. No.: 114,126

[22] Filed: Oct. 28, 1987

[51] Int. Cl.⁴ .......... A61F 5/00

[52] U.S. Cl. .......... 128/69; 128/68

[58] Field of Search .......... 128/69, 68, 62 R, 78, 128/60, 70, 44, 67, 61, 24 R

[56] References Cited

U.S. PATENT DOCUMENTS

| | | | |
|---|---|---|---|
| 726,054 | 4/1903 | Hartford | 128/69 |
| 1,398,150 | 11/1921 | Pollard | 128/69 |
| 1,904,039 | 4/1933 | Bruder . | |
| 2,026,332 | 12/1935 | Walstrom | 128/69 |
| 2,818,854 | 1/1958 | Johnson | 128/69 |
| 3,359,577 | 12/1967 | Rogers . | |
| 4,230,099 | 10/1980 | Richardson | 128/69 |
| 4,383,342 | 5/1983 | Forster . | |

*Primary Examiner*—David A. Wiecking
*Assistant Examiner*—Huong Q. Pham
*Attorney, Agent, or Firm*—Ross, Howison, Clapp & Korn

[57] ABSTRACT

A device (10, 60) for localized bone manipulation includes a base member (12, 62) and a support member (14, 64, 66). The support member (14, 64, 66) is spaced apart from the base member (12, 62) and is disposed generally parallel to the base member (12, 62) for supporting the bone being manipulated. Structure (20) extends between the base member (12) and the support member (14) for generating superiorly and anteriorly directed forces on the bone being manipulated. Structure (68, 70) extends between the base member (62) and the support member (64, 66) for generating superiorly, anteriorly, and laterally directed forces on the bone being manipulated.

5 Claims, 2 Drawing Sheets

VERTEBRAE AND RIB MANIPULATION DEVICE

TECHNICAL FIELD

This invention relates to medical treatment devices, and more particularly to a device for the localized treatment and manipulation of vertebrae and ribs.

BACKGROUND OF THE INVENTION

In treating ligamentous strains of any joint of the body such as, for example, the articular facet joints of the vertebrae and costovertebral joints between the ribs and the vertebrae, it is important that the treatment be localized to the specific area or joint that is injured to avoid straining adjacent vertebral segments or joints. In treatment of these joints, the direction and pressure applied must be specific and must be maintained with sufficient force until a release occurs, usually within minutes. Forces extended for a long period of time past the time of release are generally of no benefit and can be counterproductive. The articular facet joints of the vertebrae and costovertebral joints between the ribs and the vertebrae lend themselves to correction by maintaining a specifically directed pressure (a vector force). In treating the articular facet joints, a vector force directed anteriorly, towards the front of the body, and superiorly, towards the head, and generally in a direction along the plane of the facet joint provides favorable treatment. In treating a costovertebral joint, a vector force anteriorly, superiorly, and laterally applied to the angle of the rib achieves a favorable result.

Previously developed techniques for treating strains of spinal joints have included the use of traction devices in which traction forces are applied along the entire spine or entire regions of the spine. However, when such traction is applied, normal segments of the spine as well as abnormal segments receive traction. The abnormal areas are surrounded by paravertebral muscle spasm guarding them from motion. The normal segments are not surrounded by muscle spasm and therefore, when traction is applied to normal as well as abnormal areas, the normal areas are the first and usually only areas to move. When this movement occurs, the proprioceptive nerve fibers from these previously normal joints reflexly set up muscle spasm surrounding these joints. This creates secondary problems while not resolving the primary problem for which traction was prescribed. An additional problem noted with linear or tensil traction is that the vector force is not applied along the planes of the joints involved which is required to achieve a release.

A need has thus arisen for a device for the treatment of strains of joints of the body, and particularly joints of the vertebrae and ribs which allows for sustained localized treatment and for the generation of a more favorable vector force applied to the joint.

SUMMARY OF THE INVENTION

In accordance with the present invention, a device for localized bone manipulation of a human body is provided. The device includes a base member and a support member. The support member is spaced apart from the base member and is disposed generally parallel to the base member for supporting the bone being manipulated. Structure extends between the base member and the support member for generating a force superiorly and anteriorly directed on the bone being manipulated.

BRIEF DESCRIPTION OF THE DRAWINGS

For a more complete understanding of the present invention and for further advantages thereof, reference is now made to the following Description taken in conjunction with the accompanying Drawings in which.

DESCRIPTION OF THE PREFERRED EMBODIMENTS

Figure 1:
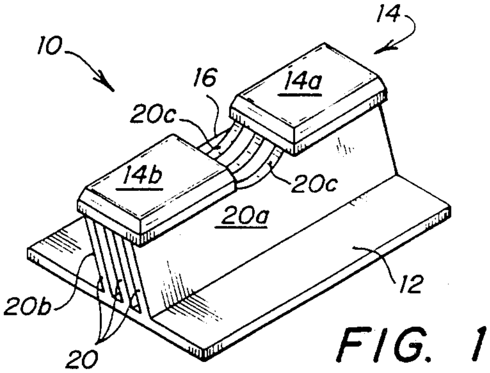
FIG. 1 is a perspective view of the present vertebral manipulating device.

Referring to FIG. 1, the present vertebral manipulating device is illustrated and is generally identified by the numeral 10. Vertebral manipulating device 10 includes a base member 12 and a support member 14. Support member 14 includes two portions, 14*a* and 14*b* separated by a gap 16. Interconnecting base member 12 and support member 14 are a plurality of spaced apart projections or veins 20. Each vein 20 includes a front surface 20*a*, back surface 20*b* and a top edge surface 20*c*. Top edge surface 20*c* disposed between support members 14*a* and 14*b* within gap 16 is concave in configuration. Veins 20 are composed of a resilient material which when flexed during use allow support member 14 to move generally parallel with respect to base member 12.

Figure 2:
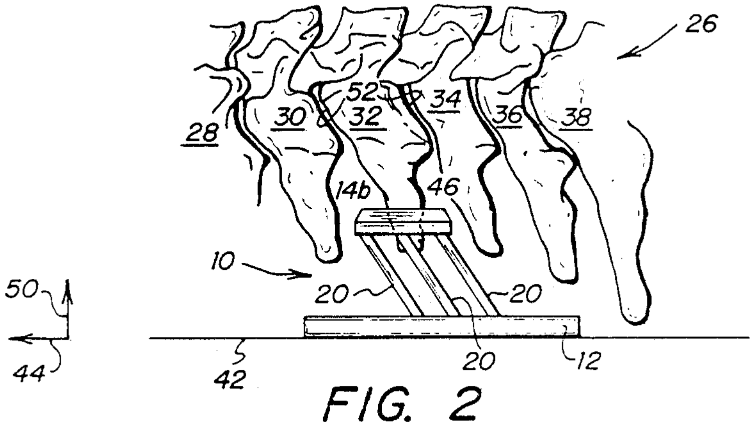
FIG. 2 is a side elevational view of a portion of the cervical spine in which muscle and skin have been deleted for clarity of illustration, illustrating the use of the present cervical manipulating device of FIG. 1.
Figure 3:
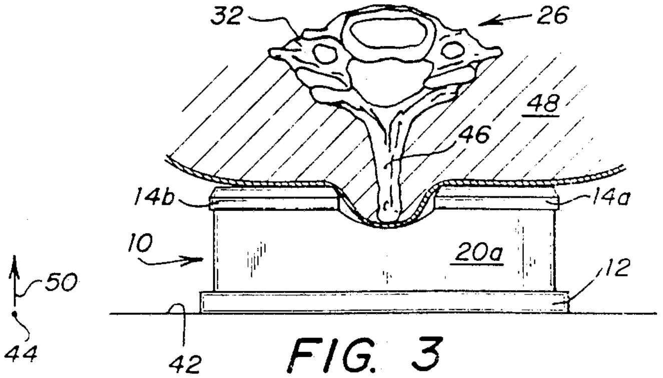
FIG. 3 is an end view of a portion of the cervical spine illustrating the use of the present vertebral manipulating device viewed from the top of a vertebrae.

Referring simultaneously to FIGS. 1, 2, and 3, vertebral manipulating device 10 is specifically shown in FIGS. 2 and 3 for use. FIGS. 2 and 3 illustrate a portion of the cervical spine, generally identified by the numeral 26. Cervical spine 26 includes a plurality of vertebrae 28, 30, 32, 34, 36, and 38. Although the present vertebral manipulating device 10 is illustrated for use in the cervical area of the spine, the present invention can be utilized to manipulate any vertebrae along the spinal column.

Vertebral manipulating device 10 is placed on a support surface such as a floor 42 or a table. The patient being treated lies with the patient's back adjacent to support member 14. Veins 20 are directed towards the head of the user as indicated by arrow 44. Vertebral manipulating device 10 is positioned adjacent vertebrae 32 being treated, such that the spinous process 46 of vertebrae 32 lies partially within gap 16 between support members 14*a* and 14*b* of support member 14. FIG. 3 illustrates the patient supported by support member 14 during use of vertebral manipulating device 10, and views vertebrae 32 from the head towards the foot of the patient and the patient's back muscle and tissue 48.

The force generated by vertebral manipulating device 10 is directed anteriorly, toward the front of the body indicated by arrow 50 and superiorly, toward the head of the body indicated by arrow 44 in a direction generally along the plane of the facet joints 52 located between vertebrae 30, 32, and 34. The resulting vector force locally treats the joints between vertebrae and thereby avoids straining adjacent segments or joints of the spinal column not needing treatment.

Figure 4:
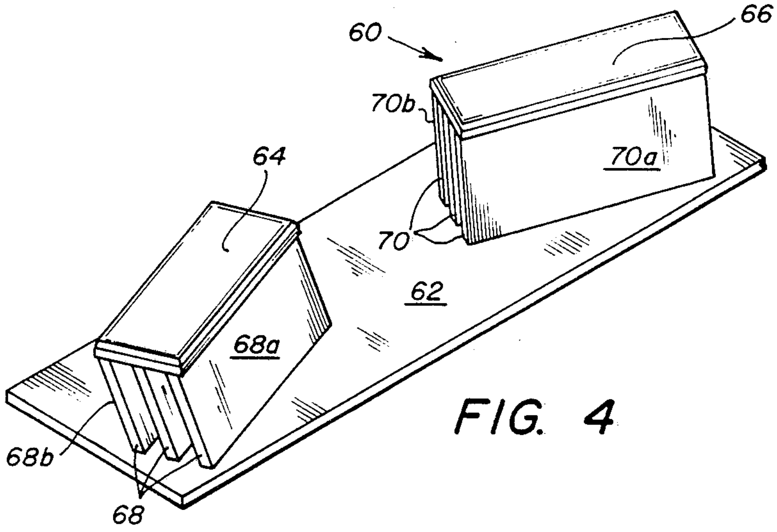
FIG. 4 is a perspective view of the present rib manipulating device.
Figure 5:
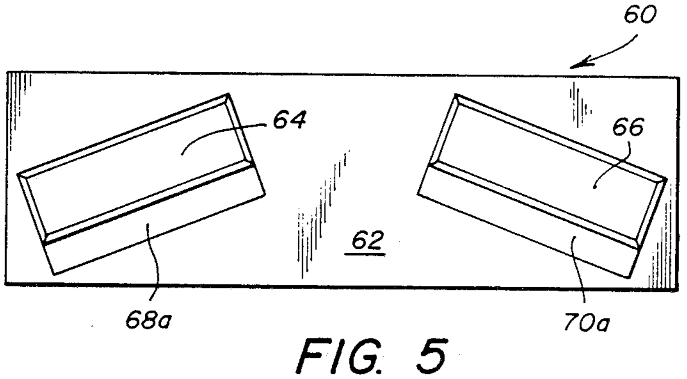
FIG. 5 is a top plan view of the rib manipulating device illustrated in FIG. 4.
Figure 6:
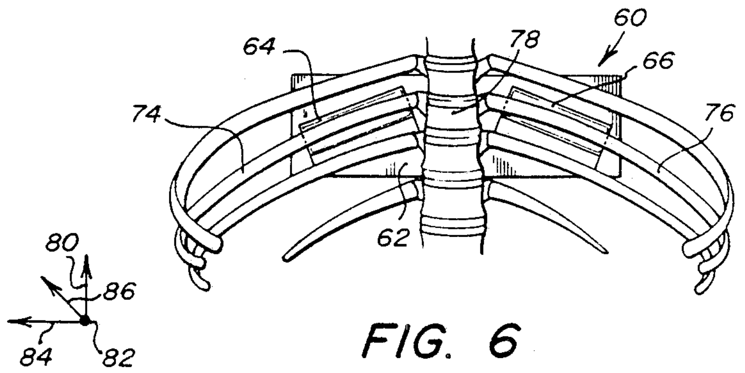
FIG. 6 is a top plan view of a portion of the spine and ribs illustrating the use of the present rib manipulating device.

Referring now simultaneously to FIGS. 4, 5, and 6, the present rib manipulating device is illustrated and is generally identified by the numeral 60. Rib manipulating device 60 includes a base member 62 and support members 64 and 66. Support member 64 is interconnected to base member 62 through a plurality of spaced apart projections or veins 68 having front and rear 20 surfaces 68*a* and 68*b*, respectively. Support member 66 is spaced apart from support member 64 and is interconnected to base member 62 using a plurality of veins 70. Veins 70 include front and rear surfaces 70*a* and 70*b*, respectively. Veins 68 and 70 are angularly disposed between base member 62 and support members 64 and 66 to direct forces anteriorly, superiorly, and laterally against the rib.

In use, as illustrated in FIG. 6, rib manipulating device 60 is placed on a support surface such as a floor 72 and the patient lies face-up on support members 64 and 66 such that support members 64 and 66 are slightly inferior and posterior to individual ribs 74 and 76 on either side of the vertebral column 78. The forces exerted on ribs 74 and 76 and their and associated joints are directed toward the head as indicated by arrow 80, toward the front of the body as indicated by arrow 82 and toward the side of the body as indicated by arrow 84 resulting in a summation vector of these three forces as indicated by arrow 86. Veins 68 and 70 are resilient to allow support members 64 and 66 to move with respect to base member 62 while rib manipulating device 60 is in use. Rib manipulating device 60 is used for local manipulation of a single rib or single pair of ribs and the associated joints.

Veins 20 of vertebral manipulating device 10 and veins 68 and 70 of rib manipulating device 60 may also be fabricated from bristle-like material or nonresilient material or as previously described a resilient material such as rubber.

It therefore can be seen that the present invention provides for the treatment of strains of joints of the body on a localized basis. Furthermore, this same concept would hold true and be applicable to use on other vertebrates.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A device for localized bone manipulation in the human body having facet joints, comprising a base member;

support spaced apart from said base member by a distance and disposed generally parallel to said base member for supporting the bone being manipulated;

force generating means extending between said base member and said support members for generating superiorly and anteriorly directed forces on the bone being manipulated; and said force generating means including a plurality of upwardly extending, spaced apart projections interconnecting said base member and said support members, said force generating means is further being flexible so as to be angularly disposed in a direction generally parallel to a plane containing the facet joints to apply a force to said support members to thereby move said support members generally parallel to said base member and in the direction toward the head of the human body, such that the distance between said base member and said support members decreases as the bone is being manipulated.

2. The device of claim 1 wherein said support members are separated by a gap for clearance of the spinous processes of vertebrae.

3. The device of claim 1 wherein said support members are first and second support members for receiving a pair of ribs being manipulated.

4. The device of claim 2 wherein said force generating means includes a concave portion in the area of said gap for clearance of the spinous processes of vertebrae.

5. The device of claim 1 wherein said force generating means comprises a rubber material.

* * * * *

UNITED STATES PATENT AND TRADEMARK OFFICE
CERTIFICATE OF CORRECTION

PATENT NO. : 4,785,801

DATED : November 22, 1988

INVENTOR(S) : Conrad A. Speece

It is certified that error appears in the above-identified patent and that said Letters Patent is hereby corrected as shown below:

Column 4, Claim 1, Line 13:

After "support" insert --members--.

Signed and Sealed this

Twenty-fifth Day of April, 1989

*Attest:*

DONALD J. QUIGG

*Attesting Officer*

*Commissioner of Patents and Trademarks*